(12) United States Patent
Bonneau, Jr. et al.

(10) Patent No.: US 8,704,660 B2
(45) Date of Patent: Apr. 22, 2014

(54) CHEMICAL-SELECTIVE DEVICE

(75) Inventors: Walter C. Bonneau, Jr., Escondido, CA (US); Jon Macklin, El Cajon, CA (US)

(73) Assignee: Cubic Corporation, San Diego, CA (US)

( * ) Notice: Subject to any disclaimer, the term of this patent is extended or adjusted under 35 U.S.C. 154(b) by 650 days.

(21) Appl. No.: 12/948,313

(22) Filed: Nov. 17, 2010

(65) Prior Publication Data

US 2011/0115464 A1  May 19, 2011

Related U.S. Application Data

(60) Provisional application No. 61/293,592, filed on Jan. 8, 2010, provisional application No. 61/262,000, filed on Nov. 17, 2009.

(51) Int. Cl.
*G08B 21/00* (2006.01)

(52) U.S. Cl.
USPC .......... 340/540; 340/825.26; 340/5.9

(58) Field of Classification Search
USPC .......... 340/540, 5.2, 3.6, 825.26, 5.52, 5.53, 340/5.8, 5.81–5.883, 5.9, 14.62, 14.66, 340/385.1
See application file for complete search history.

(56) References Cited

U.S. PATENT DOCUMENTS

| | | | |
|---|---|---|---|
| 4,821,118 A | 4/1989 | Lafreniere et al. | |
| 4,975,222 A | 12/1990 | Yoshino et al. | |
| 5,200,614 A | 4/1993 | Jenkins | |
| 5,491,326 A | 2/1996 | Marceau et al. | |
| 5,491,337 A * | 2/1996 | Jenkins et al. | 250/287 |
| 5,722,835 A | 3/1998 | Pike | |
| 5,741,984 A | 4/1998 | Danylewych-May et al. | |
| 6,073,499 A | 6/2000 | Settles | |
| 6,160,278 A | 12/2000 | Liu et al. | |
| 6,765,198 B2 | 7/2004 | Jenkins et al. | |
| 6,975,227 B1 | 12/2005 | Nishikawa et al. | |
| 7,047,829 B2 | 5/2006 | Napoli | |
| 7,109,859 B2 * | 9/2006 | Peeters | 340/539.11 |

(Continued)

FOREIGN PATENT DOCUMENTS

DE  4322274 A1  12/1995
DE  100 31 549 A1  1/2002

(Continued)

OTHER PUBLICATIONS

International Search Report and Written Opinion of PCT/US2010/057068 mailed on Jun. 27, 2011, 19 pages.

(Continued)

*Primary Examiner* — Daniel Previl
(74) *Attorney, Agent, or Firm* — Kilpatrick Townsend & Stockton LLP

(57) ABSTRACT

A smartcard or other media that detects the presence of chemical and/or biological compounds or other items of interest on individuals handling by using chemical-selective devices. These chemical-selective devices can include non-linear (e.g., diode and/or transistor) and/or time non-linear (e.g., controlled resistor) electrical components and can indicate exposure to an item of interest through a change in one or more electrical characteristics. The exposure of the chemical-selective devices to items of interest is stored such that, when the smartcard or other media is presented to a card reader, the detection data can be transmitted to the card reader for appropriate processing by the system.

22 Claims, 11 Drawing Sheets

(56) References Cited

U.S. PATENT DOCUMENTS

| | | |
|---|---|---|
| 7,139,406 B2 | 11/2006 | McClelland et al. |
| 7,171,312 B2 * | 1/2007 | Steinthal et al. .............. 702/32 |
| 7,271,720 B2 | 9/2007 | Tabe |
| 7,367,494 B2 | 5/2008 | Macklin et al. |
| 7,491,948 B2 | 2/2009 | Gordon et al. |
| 7,522,040 B2 | 4/2009 | Passmore et al. |
| 7,677,449 B2 | 3/2010 | Macklin et al. |
| 7,936,265 B2 | 5/2011 | Macklin et al. |
| 2002/0024450 A1 | 2/2002 | Townsend et al. |
| 2003/0128099 A1 | 7/2003 | Cockerham |
| 2003/0143119 A1 | 7/2003 | Schwartz et al. |
| 2004/0073439 A1 | 4/2004 | Shuster |
| 2004/0165750 A1 | 8/2004 | Chew |
| 2004/0169076 A1 * | 9/2004 | Beale et al. ................ 235/382 |
| 2004/0183153 A1 | 9/2004 | Liu et al. |
| 2004/0204915 A1 | 10/2004 | Steinthal et al. |
| 2005/0019220 A1 | 1/2005 | Napoli |
| 2005/0022581 A1 | 2/2005 | Sunshine |
| 2005/0088299 A1 | 4/2005 | Bandy et al. |
| 2005/0233366 A1 * | 10/2005 | Mino ............................ 435/6 |
| 2005/0288937 A1 | 12/2005 | Verdiramo |
| 2006/0180647 A1 | 8/2006 | Hansen |
| 2006/0243796 A1 * | 11/2006 | Macklin et al. .............. 235/382 |
| 2006/0290496 A1 | 12/2006 | Peeters |
| 2007/0102294 A1 | 5/2007 | Dorisio et al. |
| 2009/0072024 A1 | 3/2009 | Bonneau, Jr. et al. |
| 2009/0115605 A1 | 5/2009 | Ravenis, II et al. |
| 2010/0219932 A1 | 9/2010 | Macklin et al. |

FOREIGN PATENT DOCUMENTS

| | | |
|---|---|---|
| EP | 599291 A2 | 6/1994 |
| EP | 1182622 A1 | 2/2002 |
| WO | WO 03/075119 A2 | 9/2003 |
| WO | WO 2004/114242 A1 | 12/2004 |
| WO | WO 2006/035392 A1 | 4/2006 |
| WO | WO 2006/096246 A1 | 9/2006 |
| WO | WO 2006/130528 A1 | 12/2006 |
| WO | WO 2007/081922 A2 | 7/2007 |
| WO | 2008/035273 A2 | 3/2008 |

OTHER PUBLICATIONS

"Explosives and Narcotics Detection—EntryScan3" retrieved off internet http://www.geindustrial.com/ge-interlogix/iontrack/prod_entryscan.html on Dec. 2, 2005, 1 page.

"Explosives and Narcotics Detection—Itemiser3" retrieved off internet http://www.geindustrial.com/ge-interlogix/iontrack/prod_itemiser.html on Dec. 2, 2005, 1 page.

"Explosives and Narcotics Detection—StreetLab," retrieved off internet http://www.geindustrial.com/geinterlogix/iontrack/prod_streetlab.html on Dec. 2, 2005, 1 page.

"Explosives and Narcotics Detection—VaporTracer2" retrieved off internet http://www.geindustrial.com/ge-interlogix/iontrack/prod_vaportracer.html on Dec. 2, 2005, 1 page.

"Explosives and Narcotics Detection," retrieved off internet http://www.geindustrial.com/ge-interlogix/iontrack/prod_tech_overview.html on Dec. 2, 2005, 1 page.

* cited by examiner

CHEMICAL-SELECTIVE DEVICE

CROSS-REFERENCE TO RELATED APPLICATIONS

This application is related to and claims the benefit of U.S. Provisional Patent Application No. 61/262,000 filed Nov. 17, 2009 by Bonneau Jr. et al. and entitled "Chemical-Selective Device" and U.S. Provisional Patent Application No. 61/293,592 filed Jan. 8, 2010 by Bonneau Jr. et al. and entitled "Chemical-Selective Device" all of which the entire disclosures of each are incorporated herein by reference for all purposes.

This application further incorporates U.S. patent application Ser. No. 12/123,387 filed May 5, 2008 by Ravenis et al. and entitled "Smart Card Detectors" for all purposes.

BACKGROUND OF THE INVENTION

This disclosure relates in general to chemical and biological detection and, but not by way of limitation, to said detection using smartcards.

Detection of trace droplets or particles from compounds which may represent a threat to the public is based on the capture and analysis of the material. Capture may be accomplished through contact (e.g., wipe a surface or contact with a capture surface) or through capture from the atmosphere (e.g., forced air flow such as a "puffer" to dislodge particles from surfaces or through vapor sampling from the atmosphere).

Analysis in most current systems employs ion mobility spectroscopy as the mechanism for detecting items of interest. The detection capture and analysis devices may be installed in the infrastructure being protected such as at the portals for entry or exit, positioned to capture from the persons involved through contact (e.g., touch or swipe) or may be handheld and employed by those protecting the infrastructure. Such devices are common in airports today. The devices typically are slow in the capture and analysis process, frequently require operator participation and require regular cleaning, potentially after each use. In addition, the analysis results are frequently ambiguous, resulting in high false alarm rates.

An emerging class of detection devices relies on the capture of the threat indicating material causing a change in the composition of the material of the device which captures it. The change is then observable or causes a detectable change in the color or reflective photo luminescence. For example, film tags are used in nuclear facilities to determine if there has been exposure to radiation. Optical scanners may be employed to detect the change in color or luminescence when the capture material is presented.

BRIEF SUMMARY OF THE INVENTION

A smartcard or other media having integrated or internal detection can detect the presence of chemical and/or biological compounds or other items of interest on individuals handling by using chemical-selective devices. These chemical-selective devices can include non-linear (e.g., diode and/or transistor) and/or time non-linear (e.g., controlled resistor) electrical components and can indicate exposure to an item of interest through a change in one or more electrical characteristics. The exposure of the chemical-selective devices to items of interest is stored such that, when the smartcard or other media is presented to a card reader, the detection data can be transmitted to the card reader for appropriate processing by the system.

One embodiment includes an electrical device for detecting an item of interest in a detector card, the electrical device having a detection material sensitive to exposure to the item of interest. At least one surface of the detection material can be configured to be exposed to items external to the electrical device, an electrical characteristic of the detection material can be altered after exposure to the item of interest, and the item of interest can comprise a chemical and/or biologic compound. The device further can include a semiconductor material adjacent to the detection material configured to comprise part of a diode or a transistor. The device further can include a plurality of electrical terminals configured to provide electrical current through at least a portion of the detection material and the semiconductor material.

Optionally, the semiconductor material can comprise an n-type semiconductor material and a p-type semiconductor material forming a PN junction, where the detection material is adjacent to the p-type semiconductor material or the n-type semiconductor material. Furthermore, the device can include a substrate material between at least one electrical terminal and either the p-type semiconductor material or the n-type semiconductor material.

The detection material can comprise a molecularly imprinted polymer. Optionally, the electrical device can include a conductive material, in addition to the detection material, wherein the plurality of electrical terminals provide electrical current through at least a portion of the conductive material. Moreover, the conductive material can include a conductive path that enables at least a portion of the electrical current to bypass the detection material. Additionally or alternatively, the conductive material includes at least one conductive material selected from the group consisting of a conductive polymer, a carbon ink material, and a silver or aluminum ink material. Optionally, the electrical device can include filter configured to physically block certain items from contacting the detection material.

In another embodiment a detection circuit is provided for detecting exposure to an item of interest. The detection circuit can comprise a first detection device having an element sensitive to the item of interest, where the element is configured to be exposed to items external to the detection device. An electrical characteristic of the element can altered after exposure to the item of interest, and the detection circuit can detect if the element has been exposed to the item of interest. The item of interest can comprise a chemical and/or biologic compound. The detection circuit can include a second detection device that has a second element sensitive to the item of interest. The second element sensitive to the item of interest can be protected from exposure to items external to the second detection device. Finally, the detection circuit can comprise a power source electrically coupled with the first detection device.

Optionally, the power source can generate at least some of its power by inductive coupling. Additionally or alternatively, the detection circuit can have a comparator where an output of the first detection device is electrically coupled with a first input of the comparator and an output of the second detection device is electrically coupled with a second input of the comparator. The comparator can compare electrical signals of the two inputs and provide an electrical signal based, at least in part, on the comparison. Optionally, the first and second detection devices are nonlinear detection devices. The detection circuit can include a third detection device having an element sensitive to a second item of interest.

In yet another embodiment, a method of manufacturing a device for detecting an item of interest is provided. The method can include forming, on a substrate, a region of detection material sensitive to exposure to the item of interest. At least one surface of the detection material can be configured to be exposed to items external to the electrical device, and an electrical characteristic of the detection material can be altered after exposure to the item of interest. Moreover, the item of interest comprises a chemical and/or biologic compound. The method further can include forming, on a substrate, at least one region of semiconductor material adjacent to the detection material. The semiconductor material can be configured to comprise part of a diode or a transistor. The method further can include forming, on the substrate, at least one region of conductive material electrically coupled with the detection material and the semiconductor material.

Optionally, the substrate can comprise at least one material selected from the group consisting of paper, glass, steel, and plastic. Alternatively or additionally, forming the region of detection material, the at least one region of conductive material, or both, can comprise using one or more printing methods. The at least one region of semiconductor material can comprise an n-type semiconductor and a p-type semiconductor forming a PN junction where the region of detection material is physically adjacent to the p-type semiconductor or the n-type semiconductor. Moreover, the at least one region of semiconductor material can be physically located between the substrate and the region of detection material.

Additionally or alternatively, the detection material can comprise a molecularly imprinted polymer. The at least one region of conductive material can include a conductive path that enables at least a portion of the electrical current to bypass the detection material. Moreover, the conductive material can include at least one conductive material selected from the group consisting of a conductive polymer, a carbon ink material, and a silver or aluminum ink material. Finally, the method can include forming filter above the region of detection material.

DETAILED DESCRIPTION OF THE INVENTION

Figure 1A:
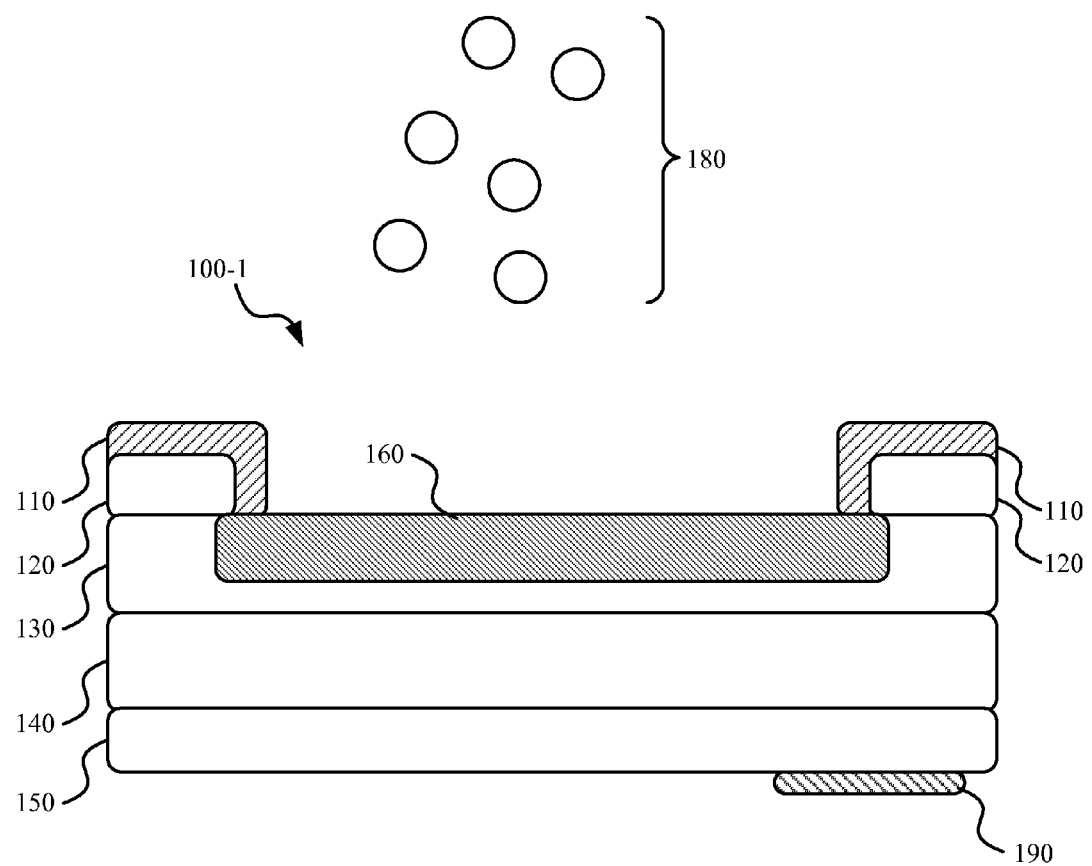
FIG. 1A is a simplified cross-sectional diagram of an embodiment of a chemical selective device for detecting particles and/or droplets of an item of interest.

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It being understood that various changes may be made in the function and arrangement of elements without departing from the spirit and scope as set forth in the appended claims.

In one embodiment, an electrical device includes a detection material, such as a polymer sensor, that captures trace particles and/or droplets from a specific threat compound (i.e. "item of interest"). The item of interest can be a particular chemical and/or biologic material. Depending on the functionality of the detection material, the threat compound may include a family of related materials.

The capture of the target particles and/or droplets changes the operation of the electrical device by changing an electrical characteristic of the detection material. According to some embodiments, the devices may have nonlinear electrical behavior. As used herein, the term "nonlinear" means non-ohmic, thereby displaying non-linear current values over a range of voltages (i.e., nonlinear I-V behavior).

Certain embodiments of electrical devices can have ohmic behavior at a given point in time but may provide a change electrical characteristics over a period of time after exposure that is not linear in nature. As used herein, the term "time nonlinear" means showing a change electrical characteristics that is not linear in nature over a period of time after exposure. A time nonlinear electrical device can include, for example, an electrical device having a ohmic resistivity after exposure, but with a resistivity that alters current in a nonlinear fashion during this time. For example, according to some embodiments, the resistivity of a time nonlinear electrical device utilizing a molecularly imprinted polymer can little or no current change for up to 4 minutes or more. However, the time nonlinear electrical device can then cause a rapid current increase from the initial value to an exposed value in a matter of seconds. According to other embodiments, the delay in current change can occur in less than 4 minutes. This delay can be a function of thickness of the detection material, among other factors.

The change of operation due to exposure of the detection material to an item of interest can be detected and/or transmitted by a circuit with which the electrical device is connected. The electrical device and/or circuit can be disposed on any of a variety of media, including cards, badges, tickets, and/or similar media used in access control or security systems, as well as media, such as boxes and other containers used in freight and/or shipping.

According to certain embodiments, a circuit can comprise one or more electrical devices with detection materials. Where multiple electrical devices are used, the detection materials of some electrical devices may detect different items of interest than the detection materials of other electrical devices. Thus, the circuit can detect any of a variety of items of interest.

According to some embodiments, a circuit can be used in systems operating at 13.56 MHz or higher with the ability to detect and report trace chemical and/or biologic material that has been in contact with the media, such as a wireless smartcard, with which the circuit is coupled. Other embodiments could use any monetary instrument, ticket, card, contactless, radio frequency identification (RFID), or token used for access and/or payment. When the media communicates with any type of access control system such as, public transit or transportation systems, automated parking systems, stadium event ticketing systems or building access systems, the trace detection status of what has come in contact with the media is reported through the infrastructure in order to provide detection, intelligence gathering information, and prevention of terrorist incidents. This information may be used for intelligence collection into a special situational awareness software program or interface into a command and control (C2) or communication, command, and control (C3) system.

A media having an electrical device using a detection material, such as but not limited to, molecularly imprinted polymer (MIP) technologies that can register detection of a substance that has come in contact with the media when in an powered or non-powered state. These technologies interact with an additional components of the electrical device to provide a detectable change in the electrical device's operation. A circuit can detect this change and provide a signal that can be relayed to a microprocessor or memory cell. The interaction can be through a chemical, physical, or electronic change. The change signifies that a detection of a threat compound or compounds has occurred. The detection event triggers changes in an electrical or data characteristic of the circuit that corresponds to the specific sensor's triggering substance. A circuit can have one or many detection sensor inputs and can be configurable to accept combinations of chemical and/or biologic substances.

A circuit can have two basic configurations, one which incorporates an integral power source and a second that is powered though induction from a electromagnetic field generated by a reader. Each configuration has the ability to detect trace materials (vapors, droplets, or particles) associated with a known compound that is or may be representative of an item of interest. Embodiments of the invention can detect the trace material and report it to a reader to deter, prevent, or contain the potential threat should it be validated. In addition to being able to detect the item of interest, some embodiments also provide an indication of the volume or strength of trace materials detected.

Detection materials, such as detection polymers, exist for many threat chemicals, as well as for various types of biologic material. Carbon nanotube, conductive and semi-conductive inks, and other nanotechnology can be used for printed electronic circuits and to interface with the detection material and/or other components of the electrical device. According to one embodiment, a circuit having one or more electrical devices for detecting a threat compound can be disposed on a smartcard that transfers the detection event data to the reader employing standard smartcard communication methods.

Detection materials, such as polymers, are currently available to detect a particular item of interest. They could include vapor or particulate sensing polymers, florescent quenching polymers, and/or Molecularly Imprinted Polymers (MIP). The molecular formula and the electrical properties for each classification of substances vary, as well as the formulations for each subclass. For example, the molecular formula for a MIP polymer that detects TNT will vary from the molecular formula for the MIP polymer that detects RDX. These differing formulas can cause the corresponding electrical properties to be different. These electrical properties can change as a function of exposure to an item of interest.

Detection materials may be used with other materials to form an electrical device for detecting an item of interest. For instance, the device may comprise conductive polymers, having conductivity levels between those of semiconductors and metals. Conductive polymers, such as but not limited to, the highly conductive Clevios™ series available from HS Starck™ can provide the base material for an electrical conversion for the detection material. The currently commercially available conductive polymers have a conductivity rating up to 1500 ohms/cm$^2$ that allows for an electromagnetic field to provide enough induced power to quantify an electrical characteristic change in the detection material.

Nanotechnology techniques, such as but not limited to, carbon nanotubes, and conductive and semiconductive silver, aluminum, or composite inks can be used to form the circuit that can discriminate the signals generated from the electrical devices having detection materials. The electrical signals can be developed through changes in inductive coupling, capacitive coupling, magnetic coupling, or resistivity, some of which are discussed in further detail below. The circuit itself, including the battery and/or the electrical device having the detection material, can be formed utilizing printed circuit printing technologies utilizing technologies such as screen printing, flexography, gravure, offset lithography, and inkjet. Additionally, the detection material, such as a detection polymer, may be formed by spin coating ink jetting, drop casting, or another method of application.

Referring initially to FIG. 1A, a simplified cross-sectional diagram of an embodiment of a electrical device having the detection material 100-1 (hereinafter referred to as a "chemical selective device" or "CSD") for detecting particles and/or droplets of an item of interest 180 is shown. According to this embodiment, a detection material 160 is provided to form a well-like structure in a semiconductor material of a first type 130 (e.g., n-type or p-type). The detection material 160 is electrically connected with one or more electrical terminals 110, which can be insulated from direct contact with the semiconductor material of the first type 130 by using a small layer of insulating material 120. The semiconductor material of the first type 130 can be formed on and/or physically adjacent to a semiconductor material of a second type 140 (e.g., p-type or n-type, having the opposite type of the semiconductor material of a first type 130). This can create a PN junction, giving the CSD 100-1 diode-like electrical behavior, with an element of variable resistivity based on exposure to an item of interest. The semiconductor material of a second type 140 can be formed on and/or physically adjacent to a substrate material 150, which can be electrically connected with an electrical terminal 190 (having opposite polarity of the electrical terminals 110).

As will be understood, this structure is compatible with various configurations. One example could be that a layer of MIP material can be formed on top of and/or adjacent to a P-type or N-type semiconductor, which can be located on top of and/or adjacent to a layer of N+-type or P-type semiconductor material. The diode can be forward biased if voltage on electrical terminals 110 is positive relative to electrical terminal 190. The substrate can comprise paper, class, steel, plastic, or any other of a variety of materials, providing that there is a conductive path to electrical terminal 190. It will be recognized that, in alternative embodiments, the detection material 160 can be applied to other components of the CSD 100-1, such as part to the substrate material 150, in the form of a coating. Such alternative embodiments may require specialized flip-chip mounting structure to ensure at least a portion of the detection material 160 is exposed to items external to the electrical device.

In operation, detection material 160 modifies the normal conductivity of semiconductor material 130 of the first type having a direct effect on the mobility factor of the electrons flowing in the CSD 100-1. Further, in the event the detection material 160 becomes exposed to particles and/or droplets of an item of interest 180, the electrical characteristics of the detection material 160 would be modified to exhibit either more or less conductivity. This can permanently modify the conductance characteristic of the detection material 160 therefore the electrical characteristics of the detection material 160 would remain changed. For example, exposure to particles and/or droplets of an item of interest 180 can change in the parametric behavior of the CSD 100-1 causing current to flow at a greater rate. According to some embodiments utilizing MIPs, a non-exposed MIPs having a small leakage current flow of, as an example, 40-60 µA where the operating voltage between electrical terminals is 2V. While an exposed MIPs to a specific substance, such as trinitrotoluene (TNT), creates greater current flow of about 500 µA at the same operating voltage. According to other embodiments, the change in current flow may be larger or smaller, depending on numerous factors, such as type of detection material 160 and/or item of interest, physical properties of the CSD 100, and more. For example, in one embodiment the current flow can be around 10 µA for an unexposed CSD 100, raising only to 17 µA when exposed. The change in current flow can occur shortly after exposure to particles and/or droplets of an item of interest 180. According to some embodiments, this can occur within 4 minutes or less from time of exposure, and can depend on the thickness of the detection material.

As with other embodiments described herein, exposure of the detection material 160 to particles and/or droplets of the item of interest 180 can cause the electrical characteristics of a CSD 100 to remain in a permanently modified (i.e., "exposed") state. Other substances coming in contact with the detection material 160 have little to no effect on the conductance of the detection material 160. As illustrated below, physical structures such as filters may be included to control the exposure of the detection material.

Figure 1B:
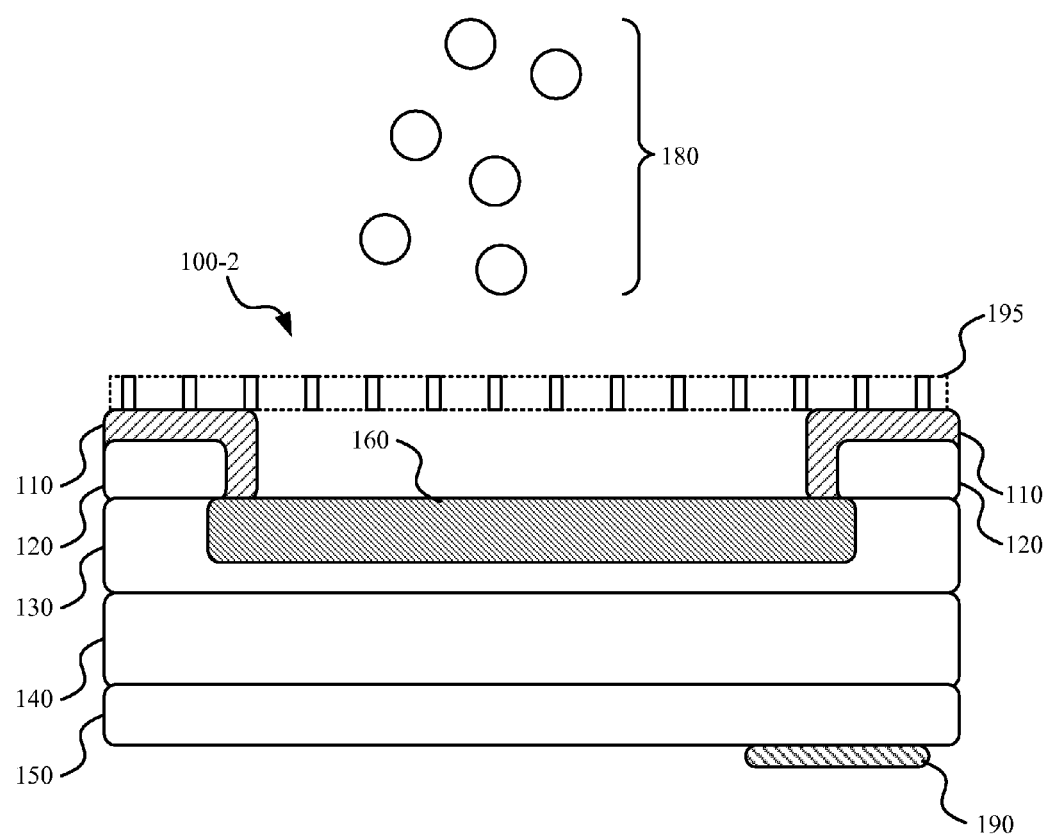
FIG. 1B is a simplified cross-sectional diagram of another embodiment of a chemical selective device for detecting particles and/or droplets of an item of interest.

FIG. 1B illustrates a simplified cross-sectional diagram of another embodiment of a CSD 100-2, similar to the CSD 100-1 of FIG. 1A. Here, however, the CSD 100-2 is configured with a filter 195 such that particles and/or droplets of an item of interest 180 must travel through the filter 195 in order to come in contact with the detection material 160. The physical characteristics of the filter 195 can depend on the known and/or anticipated size of particles and/or droplets of the item of interest 180 for which the detection material 160 is designed to detect. Although the known detection materials rarely provide false positives (i.e., react with materials other than an item of interest), such a material can provide increased accuracy. Various nanofilter technologies are contemplated by various embodiments, such as a polycarbonate or other plastic membrane.

Figure 1C:
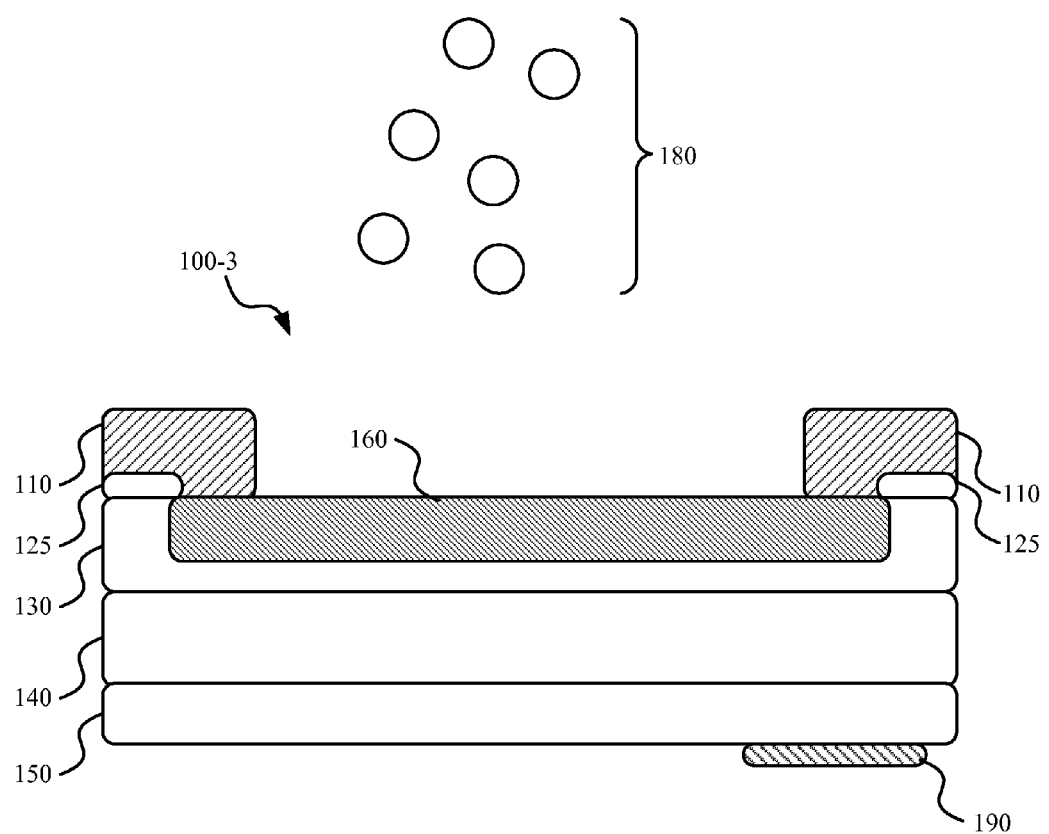
FIG. 1C is a simplified cross-sectional diagram of yet another embodiment of a chemical selective device for detecting particles and/or droplets of an item of interest.

FIG. 1C illustrates a simplified cross-sectional diagram of yet another embodiment of a CSD 100-3. Instead of insulating electric terminals 110 from the first semiconductor material 130, however, conductive channels 125 are provided. The conductive channels may have a certain resistance, thereby forming a current-restricting conductive current path enabling current flow through the PN junction. Stated another way, conductive channels 125 can limit current in a similar manner as a standard carbon resistor would restrict current flow. Also similar to a common resistor, the length, width, and thickness of the conductive channels 125 may be adjusted according to a desired minimum current flow. Conductivity also depends on the composition of the conductive channels 125, which can include a variety of materials, including conductive polymers and carbon or silver ink material. Depending on the electrical characteristics of the detection material 160, conductivity of the detection material 160 will increase or decrease after exposure to an item of interest, thereby causing a corresponding change in current flow through the device.

Figure 2:
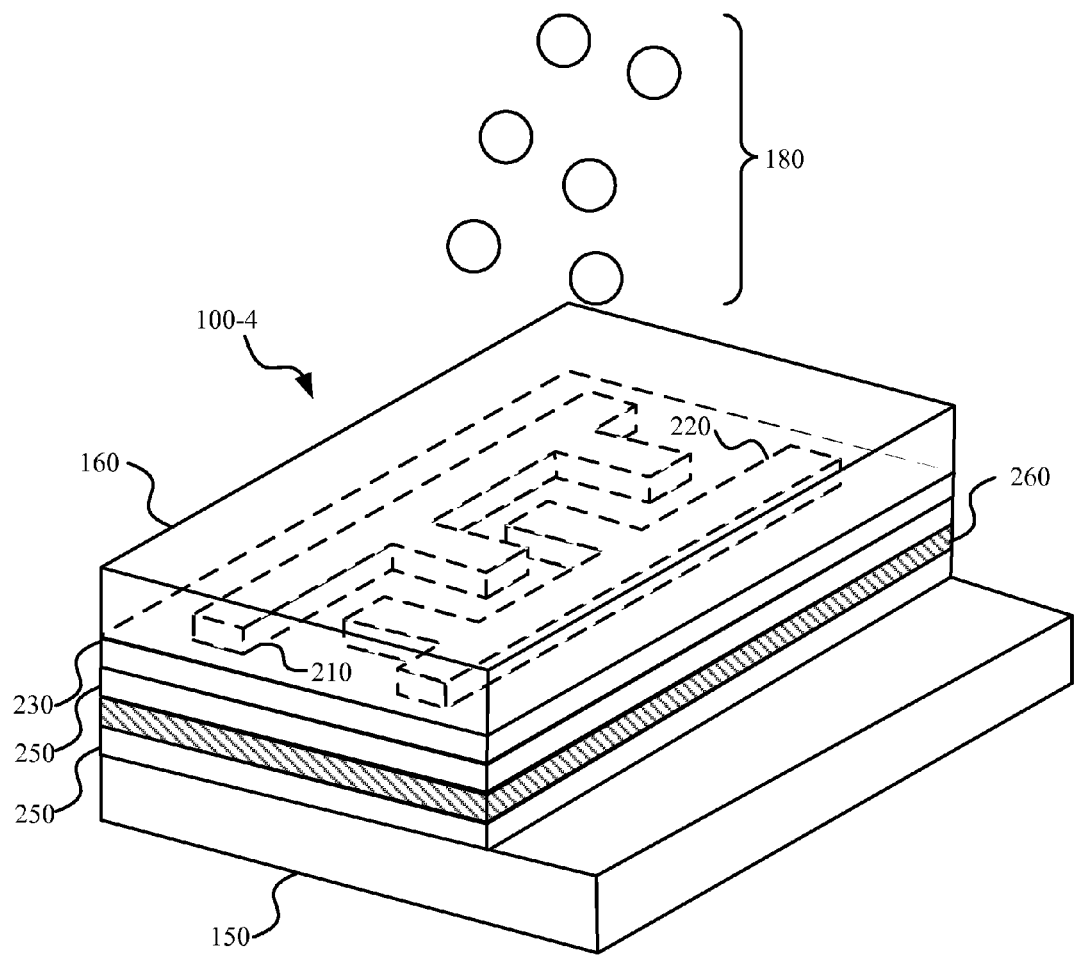
FIG. 2 is an illustration of a perspective view of an embodiment of a chemical selective device comprising a field oxide transistor (FET).

FIG. 2 is an illustration of a perspective view of an embodiment of an CSD 100-4 including a field oxide transistor (FET). This illustration shows how various components of an CSD 100-4 can be layered, depending on desired functionality and manufacturing techniques. In this same manner, more or less layers may be included in other embodiments.

The CSD 100-4 can comprise traces 210, 220 of a conductive material (providing electrical terminals), a detection material 160, and a substrate material 150. Additionally, the CSD 100-4 can include a semiconductor layer 230, a conductive gate layer 260, and insulating (e.g., dielectric) layers to electrically insulate the conductive gate layer 260 from the semiconductor layer 230 and the substrate material 150. According to some embodiments, gate may comprise and/or be embedded in the substrate material 150.

According to this embodiment, the CSD 100-4 can operate by providing an electrical voltage between traces 310, 320, which can comprise silver and/or other conductive materials. The traces 310, 320 can be interdigitated according to desired electrical operation, which can depend on the thickness of the detection material 160, spacing and thickness of the traces 310,320, and other factors. Electrical current can flow from one trace to the other via semiconductor material 230, depending on any activation voltage provided at the conductive gate layer 160. Additionally, electrical current can flow through at least a portion of the detection material 160, which is configured to be exposed to items external to the CSD 100-5, such as particles and/or droplets of the item of interest 180. Thus, the CSD 100-4 can have transistor functionality, acting as a dual-gate FET where one gate is activated by voltage while the other is activated by exposure to an item of interest.

Figure 3:
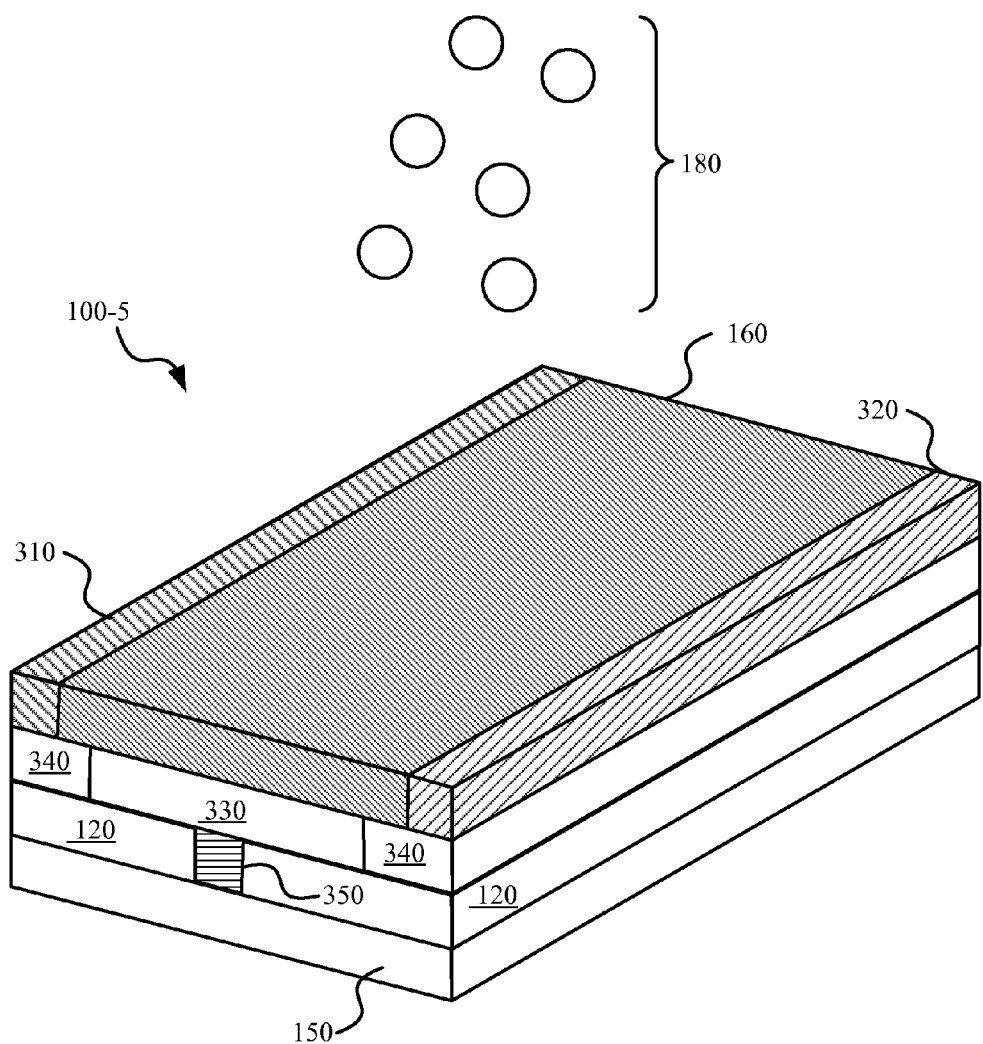
FIG. 3 is an illustration of a perspective view of an embodiment of a chemical selective device that includes a simple bipolar junction transistor (BJT).

FIG. 3 is an illustration of a perspective view of an embodiment of an CSD 100-5 that includes a simple bipolar junction transistor (BJT). Similar to the CSD 100-4 of FIG. 2, the CSD 100-5 pictured in FIG. 3 comprises detection material 160 and a substrate material 150. Additionally, the CSD 100-5 in this embodiment includes regions of semiconductor material of a first type 340, a region of semiconductor material of a second type 330, insulating material 120, and electric terminals 310,320,350. Also similar to the CSD 100-4 of FIG. 2, the CSD 100-5 pictured in FIG. 3 provides transistor functionality. According to this embodiment, PN junctions between regions of semiconductor material of a first type 340 and the region of semiconductor material of a second type 330 provide BJT functionality that can be bypassed depending on the conductivity of the detector material 160, which can change with exposure to an item of interest. Other embodiments are contemplated where the detection material 160 electrically connects other terminals of the BJT (e.g., base to emitter and base to collector) and/or is isolated to one terminal (e.g., is connected in series).

Figure 4A:
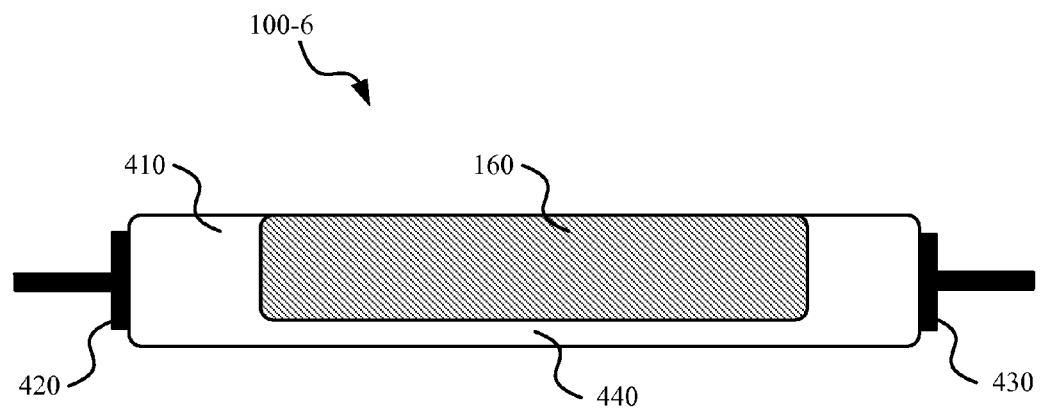
FIGS. 4A and 4B are illustrations yet other embodiments of a chemical selective device.

FIG. 4A illustrates a simplified diagram of another embodiment of a CSD 100-6 for detecting particles and/or droplets of the item of interest 180. Depending on manufacturing techniques and desired functionality, the illustration can illustrate a cross-sectional view or an overhead view, among others. As with embodiments shown above, this CSD 100-6 can include a layer and/or other region of detection material 160. The CSD 100-6 is configured such that electrical current can flow from electrical terminal 420 to electrical terminal 430 and/or vice versa.

Detection material 160 can be used with a conductive material 410 to form a current-restricting conductive current path 440 of conductive material 410 to enable current flow between electrical terminals 420, 430. The conductive current path 440 can limit current in a similar manner as a standard carbon resistor would restrict current flow. Also similar to a common resistor, physical dimensions such as length, width, and thickness of the conductive current path 440 may be adjusted to allow a desired minimum current flow. The composition of the conductive material can include a variety of materials such as conductive polymers and carbon, silver, and/or aluminum inks. The conductivity of the material(s) used will be a factor in determining proper dimensions of the conductive current path 440 for a desired minimum current flow. Depending on the electrical characteristics of the detection material 160, conductivity of the detection material 160 will increase or decrease after exposure to an item of interest, thereby causing a corresponding change in current flow from one electrical terminal to the other.

Figure 4B:
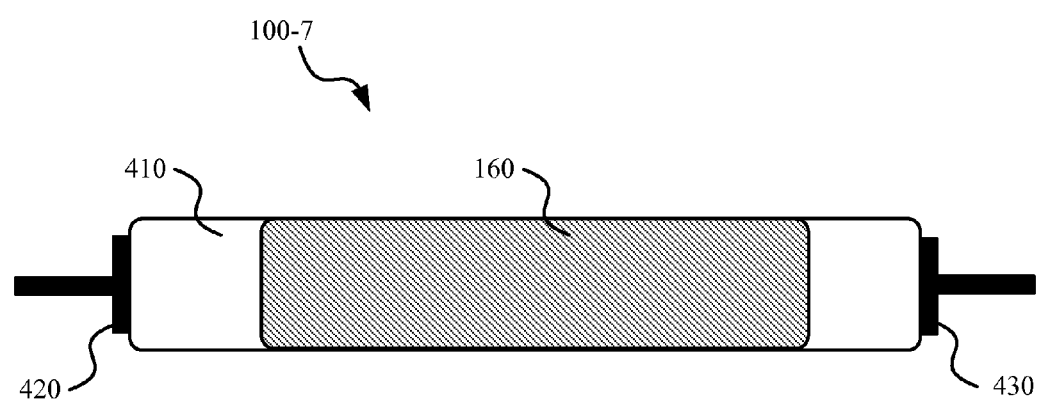

FIG. 4B illustrates a simplified diagram of yet another embodiment of a CSD 100-7. Similar to the CSD 100-6 of FIG. 4A, this CSD 100-4 is comprised of detection material 160 and conductive material 410. However, this embodiment does not include a current-restricting conductive current path 440 of conductive material 410. Instead, electrical current must flow though detection material 160. The functionality of CSD 100-7, however, is similar to CSD 100-6 in that the current is limited or increased by the change in conductance of the detection material 160, caused by exposure to particles and/or droplets of the item of interest 180. Other substances coming in contact with the detection material 160 have little to no effect on the conductance of the detection material 160. As with other embodiment discussed herein, exposure of the detection material 160 to particles and/or droplets of the item of interest 180 can cause the electrical characteristics of the device 100-4 to remain in this permanently modified (i.e., "exposed") state. CSDs 100-6 and 100-7 of FIGS. 4A and 4B, respectively, can comprise time nonlinear electrical devices, as defined above.

Figure 5:
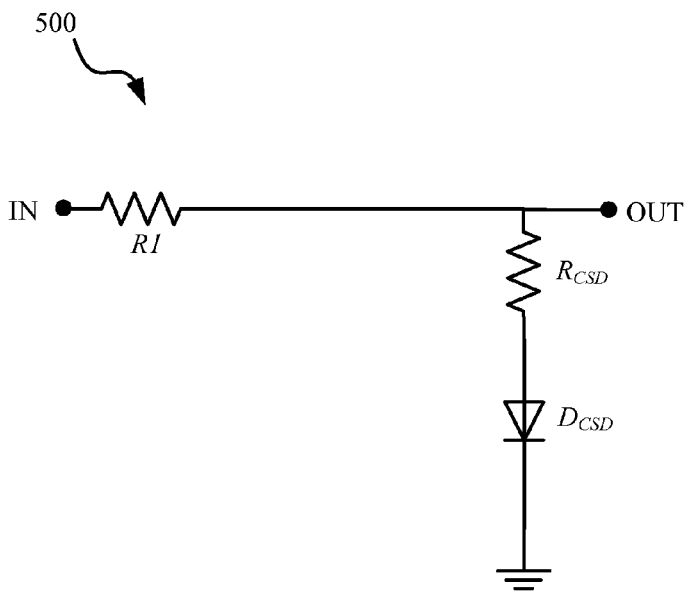
FIG. 5 illustrates an embodiment of a simple voltage divider circuit utilizing a chemical selective device.

It will be understood that the embodiments described above can be used in a variety of circuits, including circuits that function primarily to perform operations other than detect items of interest. Moreover, as discussed earlier, circuits may detect changes in inductive coupling, capacitive coupling, magnetic coupling, or resistivity. In FIG. 5, an embodiment of a simple voltage divider circuit 500 is shown, illustrating how a change in resistivity of a diode-based CSD 100 (such as CSD 100-1, shown in FIG. 1) can be measured by a change in output voltage. (Diode and resistive components of such as diode-based CSD are shown as $D_{CSD}$ and $R_{CSD}$, respectively.) The resistor R1 can be chosen in relation to $R_{CSD}$ to provide a desired range of output voltage. Of course, alternative embodiments can include other types of CSDs 100, such as resistive CSDs 100-6, 100-7, which would omit the diode component $D_{CSD}$ from the circuit.

Figure 6:
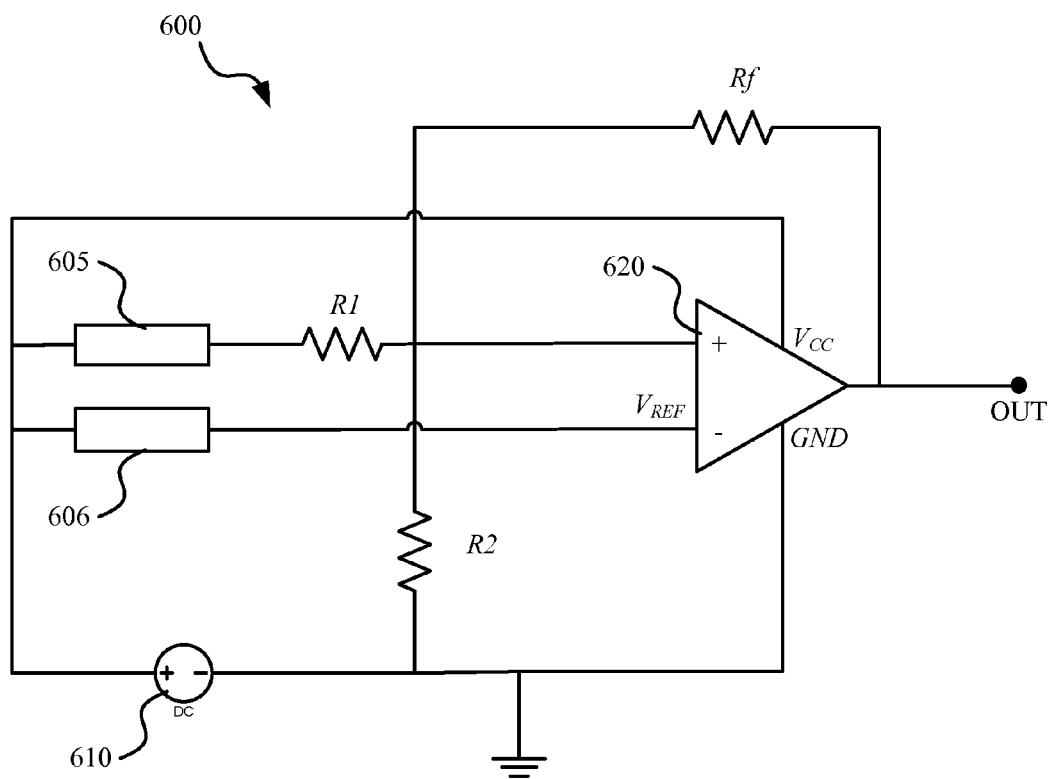
FIG. 6 illustrates an embodiment of a circuit utilizing a power supply and a comparator to provide an output signal when exposure is detected.

FIG. 6 illustrates an embodiment of a sensor circuit 600 utilizing a power supply 610 and a comparator 620 to provide an output signal when exposure is detected. Active sensing unit 605 can alter an output voltage based on expose to an item of interest and can comprise a CSD 100 and/or a circuit based on a CSD 100, such as circuit 500 of FIG. 5, depending on the functionality of the corresponding CSD 100. The output of the active sensing unit 605 is electrically connected with a first input of the comparator 620, and the output of a reference sensing unit 606 is electrically connected with a second input of the comparator 620. The reference sensing unit 606 has similar features and detection material 160 as the active sensing unit 605, but is configured to prohibit the detection material 160 from being exposed to particles and/or droplets of the item of interest 180. The reference sensing unit 606 can, for example, include a passivation layer covering the detection material 160. Thus, the reference sensing unit 606 can provide a control by which the active sensing unit 605 can be measured. According to the illustrated embodiment, resistors R1, R2, and Rf may be selected to set comparator's rising threshold voltage, $V_{THR}$, and falling threshold voltage, $V_{THF}$, which can be calculated as follows:

$$V_{THR} = V_{REF} \times R1 \left( \frac{1}{R1} + \frac{1}{R2} + \frac{1}{Rf} \right)$$

$$V_{THF} = V_{THR} - \frac{R1 \times V_{CC}}{Rf}.$$

Power supply 610 can comprise any of various types of power sources. As shown, it may comprise a battery. For systems utilizing printed electronics technology to print the circuit 600, the battery may be printed using current thin film technologies. Additionally or alternatively, the battery may be coupled with the circuit after the circuit's manufacture. Moreover, where the circuit 600 is intended for use in systems exposed to RF fields, such as a circuit on a wireless smart card exposed to an RF field of a card reader, the power source may comprise, in whole or in part, an inductive coil that supplies power when exposed to the RF field. In such systems, energy from a reader's RF field is coupled to the inductive coil and converted into appropriate voltages by the RFID circuit, providing enough power to enable circuitry to become fully functional.

Figure 7A:
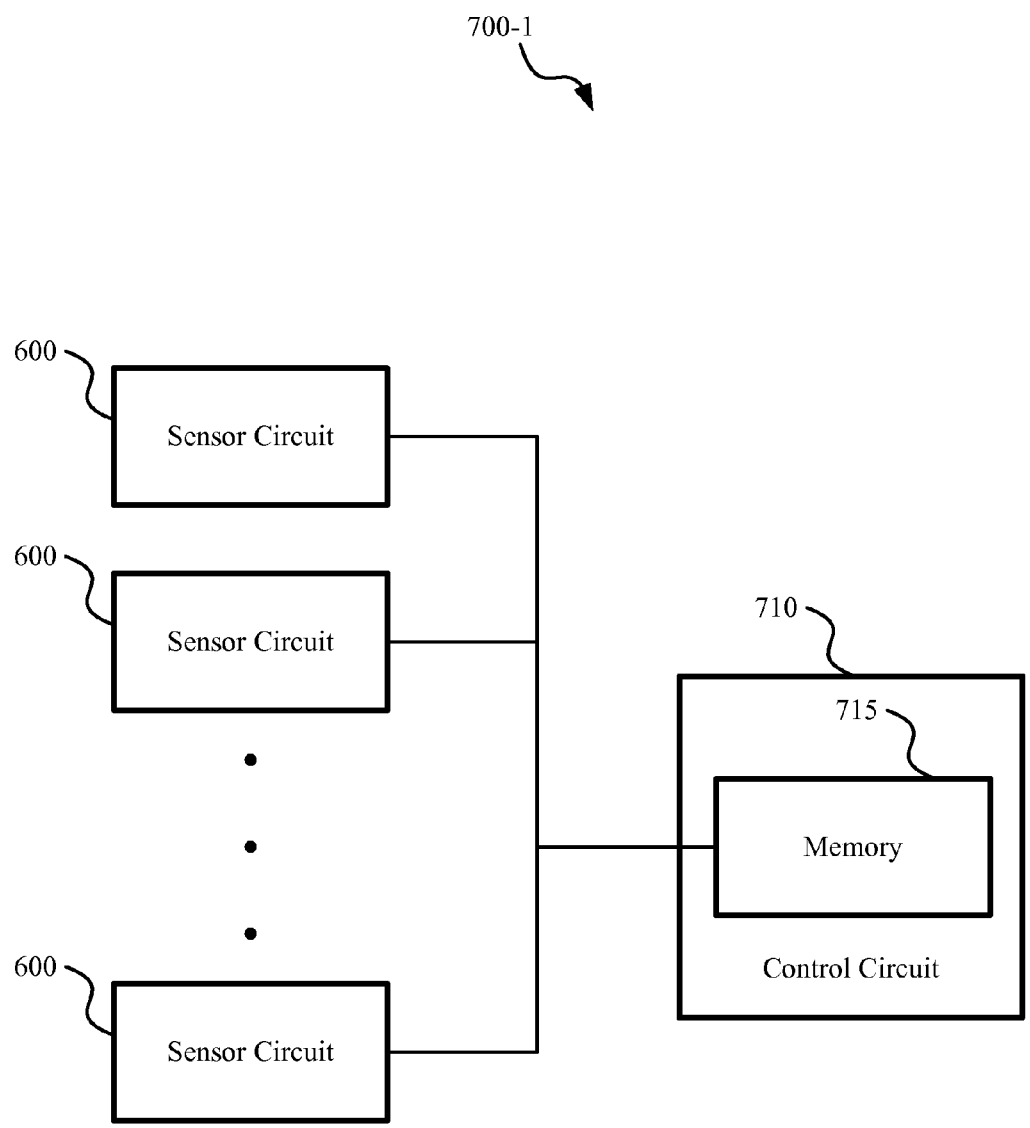
FIG. 7A is a block diagram illustrating the use of several sensor circuits as components in a system circuit, according to one embodiment.

FIG. 7A is a block diagram illustrating the use of several sensor circuits 400 as components in a system circuit 700-1, according to one embodiment. Each of the multiple sensor circuits 600 each can be configured to detect a different type of item of interest, thereby enabling the system circuit to detect a variety of items of interest. The sensor circuits 600 can be electrically connected with a control circuit 710. The control circuit 710, which can comprise a modified ISO/IEC 14443 Circuit 710 to provide functionality to contactless payment cards, can include a memory 715 to which detection information from sensor circuits 600 may be written, according to some embodiments.

Additionally or alternatively, the multiple sensor circuits 600, individually or collectively, can include a plurality (e.g., an array) of CSDs 100 configured to detect the same item of interest. This can be embodied using single or varying types of devices and/or polymer materials. Such redundancy can be used for accuracy of detection. In particular, having an plurality of electrical devices 100 configured to detect the same item of interest can provide a higher degree of granularity by which the item of interest may be measured. For example, if 5% of the electrical devices 100 indicate exposure to an item of interest, it may be caused by defects in the electrical devices 100 and therefore not a concern. The control circuit 710 may therefore not record and/or transmit the detection. On the other hand, if 30% or 50% of CSDs 100 indicate exposure to an item of interest, it may be considered a legitimate threat and thus treated as such by the system circuit 700. For example, the system circuit 700 can record and/or transmit to devices and/or systems of authoritative agencies (e.g., transit, government, etc.) where appropriate action can be taken. Other factors can be taken into account as well, such as time and/or location of electrical devices 100 indicating exposure to an item of interest.

Figure 7B:
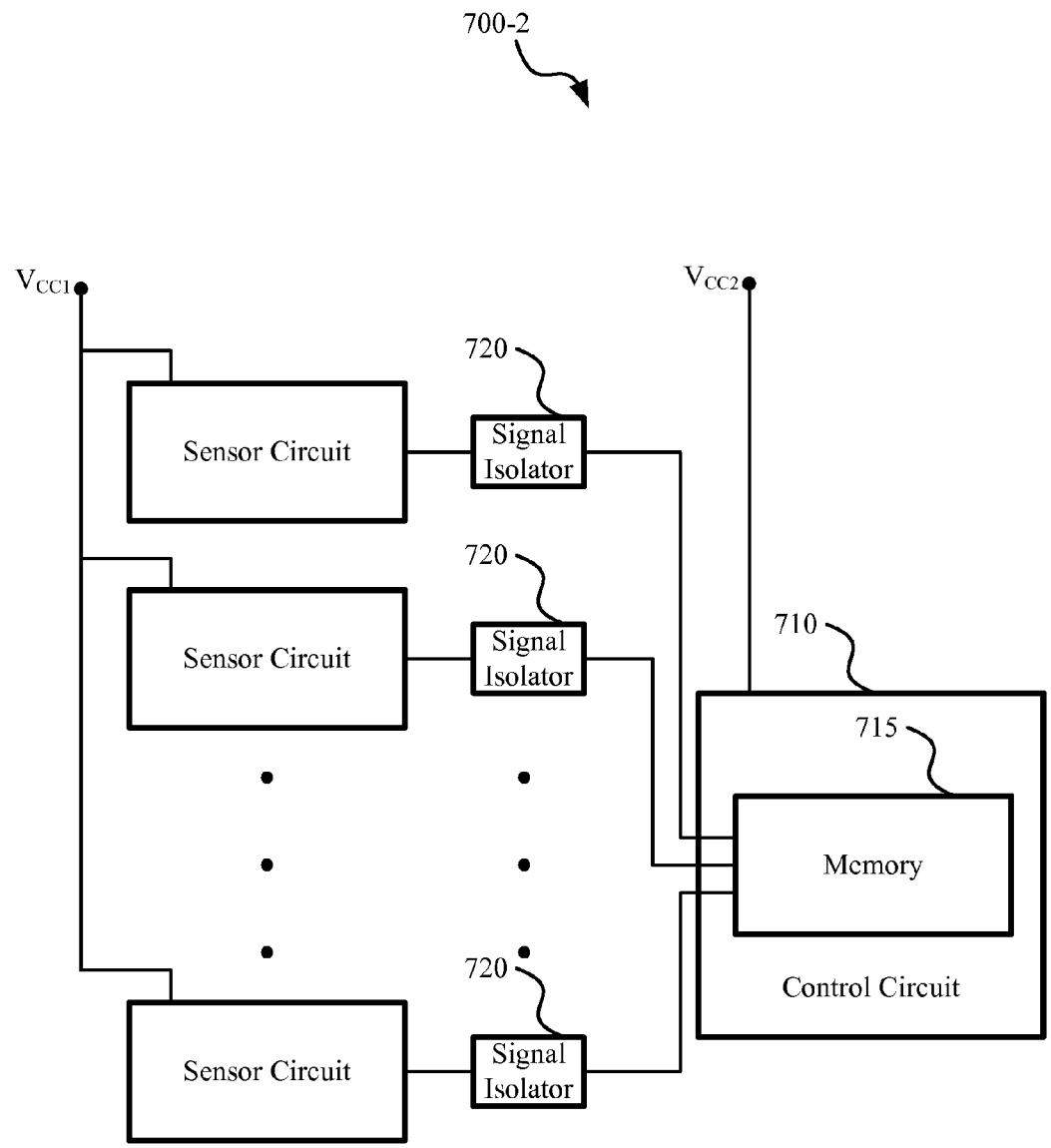
FIG. 7B is a block diagram illustrating an alternative configuration of a system circuit, according to some embodiments.

FIG. 7B is a block diagram illustrating an alternative configuration of a system circuit 700-2. First, because sensor circuits 400 can have different power requirements than a control circuit (e.g., $V_{CC1}$ and $V_{CC2}$ shown in FIG. 7A), detection information may be communicated through signal isolators 720, such as optoisolators, to preserve the electrical integrity of the circuits without forfeiting information. Second the signals from each sensor circuit (or, alternatively, each group of sensor circuits) may be separated. The separation of signals can allow the information to be written separately in memory 715 and indicate to a control circuit 710 more information about a threat (e.g., what type of detected substance it is). It will be understood, however, that a single power supply 510 can provide all circuitry on a media with power.

Figure 8:
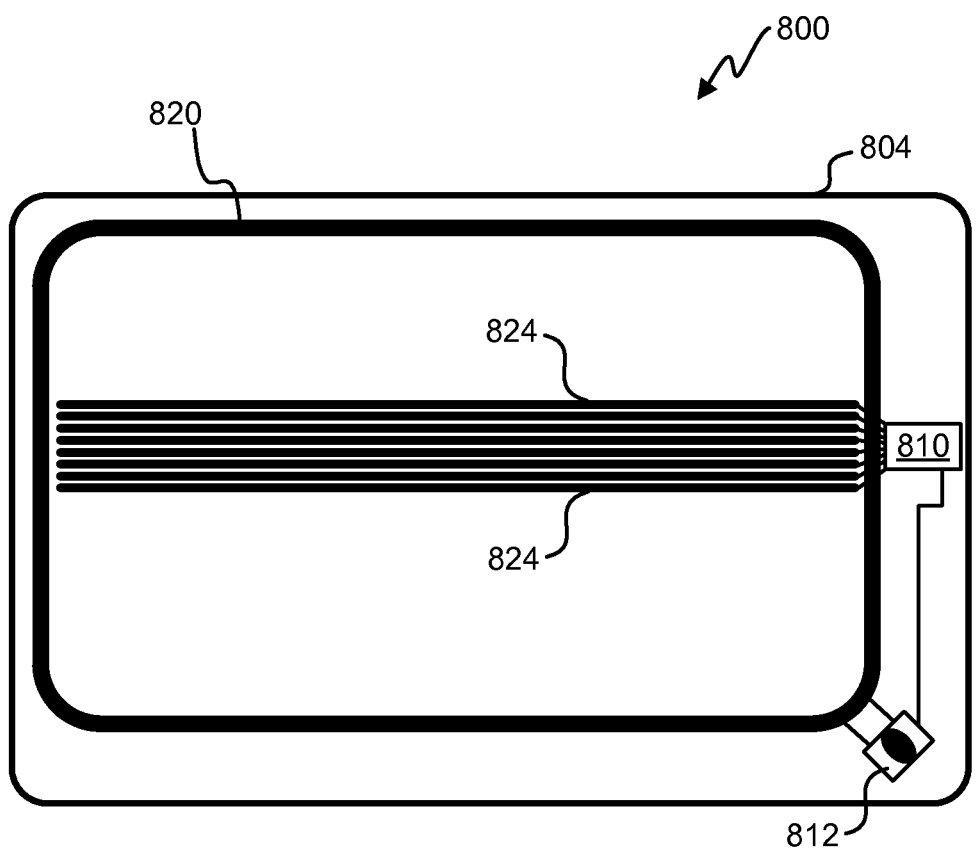
FIG. 8 shows a structural diagram of an embodiment of a detector card with chemical selective devices configured in detection stripes.

Referring next to FIG. 8, a structural diagram of an embodiment of a detector card 800 utilizing a detector circuit is shown. The configuration can be changed dependent upon the requirements of the media in which the CSDs 100 will be embedded and the ergonomics of the device to enhance detection from the expected handling of the detector card 800. The body of the card 804 can be made of a plastic, plasticized polyvinyl, glass, steel, or paper material in which CSDs 100 are disposed in an interlaced or checkered pattern, for example. This pattern can vary with ergonomic requirements.

The detector card 800 may be a token or credential (e.g., badge, ID card, license, etc.), a bank card (e.g., credit, debit, stored value, etc.), or a preferred customer or member card or a prepaid card for other economic applications (e.g., transit system fares, NFC enabled cellular phone, prepaid gift cards, etc.). The detector card or media can fit within the palm of a human hand, but other embodiments could be less than 10, 8, 6, 5, 4, 3, 2, or 1 in$^2$ and thinner than 10, 8, 6, 5, 4, 3, 2, or 1 mm. As indicated elsewhere herein, however, CSDs 100 may be embedded in any number of materials and/or devices. For example, one embodiment can comprise at least one CSD embedded in cardboard, such as box used in shipping.

According to the embodiment illustrated in FIG. 8, a plurality of CSDs 100 are arranged in a pattern of detection stripes 824 electrically connected with integrated circuit (IC) 810 that can provide functionality for detecting and/or recording exposure information. Other embodiments can include any of a number of sensitive areas or patterns of CSDs. The IC 810 can include memory 715 as well as other features such as a processor, persistent storage, and a power supply 812. Moreover, the IC 810 can be connected to an antenna 820 through a wireless transceiver. The IC 810, wireless transceiver, and antenna 820 not only can power and operate the detection circuitry, but it can also communicate information, such as detection data stored on the memory 715 wirelessly to a card reader. In turn, a card reader can transmit or send detection information to an authoritative agency for an appropriate response.

This and other embodiments described herein have passive sensors CSDs that do not require power to record exposure to items of interest. For example, MIPs technology reports detection of an item of interest that has come in contact with the MIPs when the IC 810 is in a powered or non-powered state. The detection stripes 824 or other detection sensitive areas or patterns can read a chemical, physical, or electronic change in the MIPs material. The change signifies that a detection of an item of interest (e.g., target substance or substances) has occurred. CSD 100 with which the detection stripes 824 are formed can be configured to be sensitive to one or more compounds or conditions.

Figure 9:
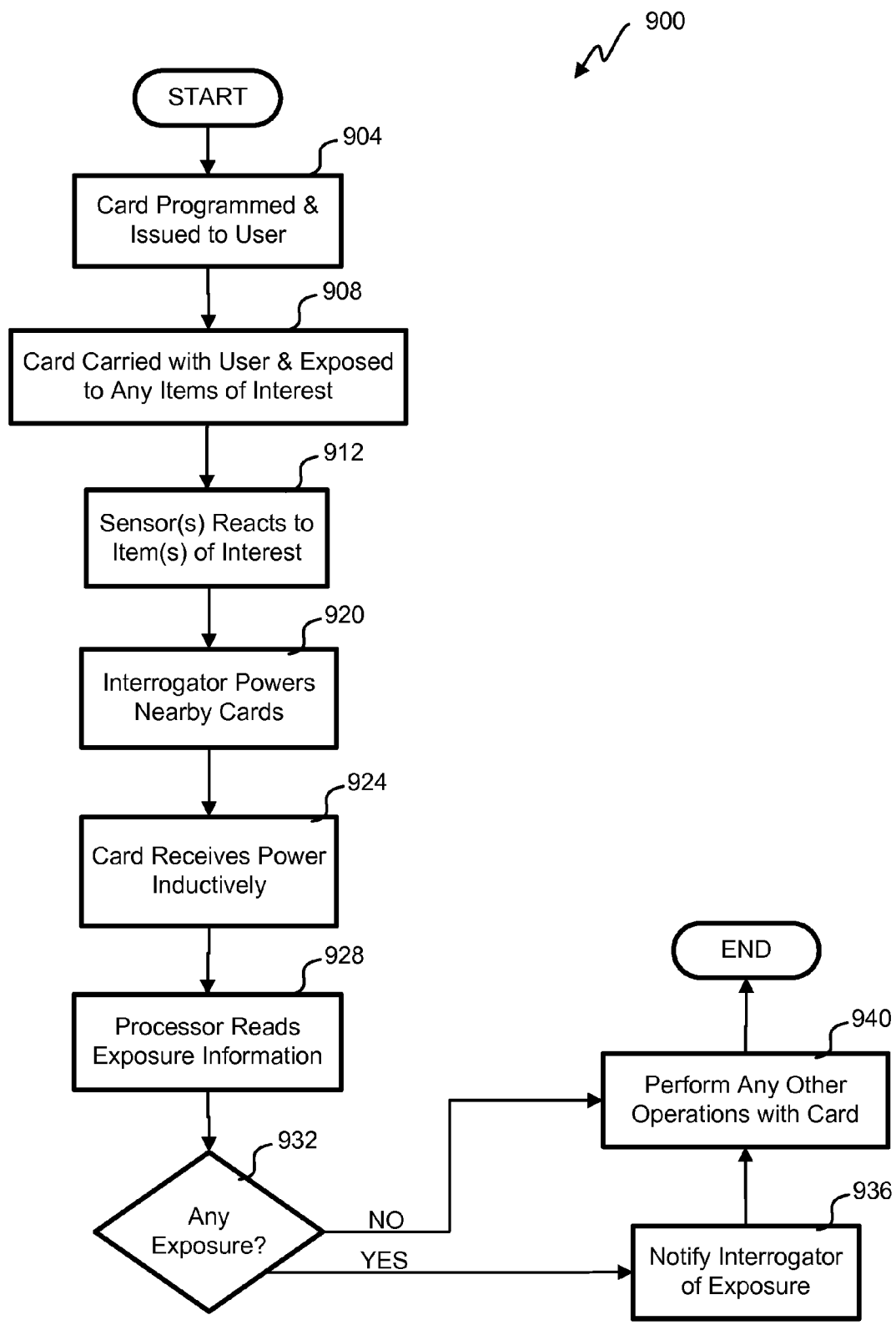
FIG. 9 a flowchart of an embodiment of a process for detecting items of interest with a detector card.

With reference to FIG. 9, a flowchart of an embodiment of a process 900 for detecting items of interest with a detector card 800 is shown. The depicted portion of the process 900 begins in block 904 where the detector card is issued to a user along with any programming. For example, the detector card 800 could be written with information the user, applications, user preferences, serial numbers, and/or other information. The user carries around the detector card 800 where it potentially is exposed to items of interest in block 908.

In block 912, the CSD 100 reacts to exposure to the relevant item(s) of interest. Any exposure is remembered as exposure information. The exposure information maybe stored in the detection material 160 using a detection polymer, for example, or some other material sensitive to the item(s) of interest.

At some point, the detector card 800 comes in contact with a card reader in block 920 that powers the coil 820 of the detector card 800 to power up the detector circuit 810 in block 924. The processor reads detection information of one or more CSDs 100 in block 928. The detection material 160 remembers the exposure, which can be read at any time as detection information. The detection information could be a range of values.

Where there is exposure detected in block 932, the card reader is sent the exposure information wirelessly in block 936. Processing continues from block 936 to block 940 where any other operations are performed with the detector card 800. Where exposure hasn't been detected, processing goes from block 932 to block 940 to perform any other operations with the detector card 800 that the card reader might perform.

It will be understood that physical devices such as key fobs and cell phones may also have conductive material 160 applied to allow detection of items of interest. The application of the detection material can be done using multiple methods, such as a polymer/nanotech ink, using a spray method, brushing, spin-coating, printing, and/or roller-coating. Ink jet printing technology can be used, for example, to spay apply the polymer to the surface or substrate.

A number of variations and modifications of the disclosed embodiments can also be used. For example, many embodiments discuss use of a smartcard or card. The invention is not meant to be so limited and could be embedded into automobile parts, handbags, shoes, belts, other clothing, hats and helmets, weapons, equipment, laptops, cooking utensils, cell phones, inventory, shipping boxes and containers, or any other portable items. Embodiments could be embedded into any human-transported item. The above embodiment describe use with a contactless smartcard, but other embodiments could use a smartcard with contacts.

While the principles of the disclosure have been described above in connection with specific apparatuses and methods, it is to be clearly understood that this description is made only by way of example and not as limitation on the scope of the disclosure.

What is claimed is:

1. An electrical device for detecting exposure to an item of interest in a detector card, the electrical device comprising:
   a detection material sensitive to exposure to the item of interest in particulate or droplet form, wherein:
   at least one surface of the detection material is configured to be exposed to items external to the electrical device, an electrical characteristic of the detection material is altered after exposure to the item of interest, and the item of interest comprises a chemical and/or biologic compound;

a semiconductor material, wherein:

the semiconductor material is adjacent to the detection material, and the semiconductor material is configured to comprise part of a diode or a transistor; and a plurality of electrical terminals configured to provide electrical current through at least a portion of the detection material and the semiconductor material, wherein the detection material is directly electrically connected with one or more of said plurality of electrical terminals.

2. The electrical device for detecting the item of interest recited in claim 1, wherein the semiconductor material comprises an n-type semiconductor material and a p-type semiconductor material forming a PN junction wherein:

the detection material is adjacent to the p-type semiconductor material, or the detection material is adjacent to the n-type semiconductor material.

3. The electrical device for detecting the item of interest recited in claim 2, further comprising a substrate material between at least one electrical terminal and either the p-type semiconductor material, or the n-type semiconductor material.

4. The electrical device for detecting the item of interest recited in claim 1, wherein the detection material comprises a molecularly imprinted polymer.

5. The electrical device for detecting the item of interest recited in claim 1, further comprising a conductive material, in addition to the detection material, wherein the plurality of electrical terminals provide electrical current through at least a portion of the conductive material.

6. The electrical device for detecting the item of interest recited in claim 5, wherein the conductive material includes a conductive path that enables at least a portion of the electrical current to bypass the detection material.

7. The electrical device for detecting the item of interest recited in claim 5, wherein the conductive material includes at least one conductive material selected from the group consisting of:

a conductive polymer, a carbon ink material, and a silver or aluminum ink material.

8. The electrical device for detecting the item of interest recited in claim 1, further comprising a filter configured to physically block certain items from contacting the detection material.

9. A detection circuit for detecting exposure to an item of interest, the detection circuit comprising:

a first detection device having a first element sensitive to the item of interest, wherein:

the first element is configured to be exposed to items external to the first detection device, an electrical characteristic of the first element is altered after exposure to the item of interest, the first detection device can detect if the first element has been exposed to the item of interest, and the item of interest comprises a chemical and/or biologic compound; and a second detection device that includes a second element sensitive to the item of interest, wherein the second element sensitive to the item of interest is protected from exposure to items external to the second detection device; and a power source electrically coupled with the first detection device and the second detection device.

10. The detection circuit for detecting exposure to an item of interest recited in claim 9, wherein the power source generates at least some of its power by inductive coupling.

11. The detection circuit for detecting exposure to an item of interest recited in claim 9, further comprising a comparator wherein:

an output of the first detection device is electrically coupled with a first input of the comparator;

an output of the second detection device is electrically coupled with a second input of the comparator; and the comparator compares electrical signals of the first and second inputs and provides an electrical signal based, at least in part, on the comparison.

12. The detection circuit for detecting exposure to an item of interest recited in claim 9, wherein the first and second detection devices are nonlinear detection devices.

13. The detection circuit for detecting exposure to an item of interest recited in claim 9, wherein the item of interest is a first item of interest, further comprising a third detection device having an element sensitive to a second item of interest.

14. A method of manufacturing a device for detecting an item of interest, the method comprising:

forming, on a substrate, a region of detection material sensitive to exposure to the item of interest in particulate or droplet form, wherein:

at least one surface of the detection material is configured to be exposed to items external to the device, an electrical characteristic of the detection material is altered after exposure to the item of interest, and the item of interest comprises a chemical and/or biologic compound;

forming, on the substrate, at least one region of semiconductor material, wherein:

the semiconductor material is adjacent to the detection material, and the semiconductor material is configured to comprise part of a diode or a transistor; and forming, on the substrate, at least one region of conductive material electrically coupled with the detection material and the semiconductor material, wherein the detection material is directly electrically connected with the at least one region of conductive material.

15. The method of manufacturing the device for detecting the item of interest recited in claim 14, wherein the substrate comprises at least one material selected from the group consisting of:

paper, glass, steel, and plastic.

16. The method of manufacturing the device for detecting the item of interest recited in claim 14, wherein forming the region of detection material, the at least one region of conductive material, or both, comprises using one or more printing methods.

17. The method of manufacturing the device for detecting the item of interest recited in claim 14, wherein the at least one region of semiconductor material comprises an n-type semiconductor and a p-type semiconductor forming a PN junction wherein:

the region of detection material is physically adjacent to the p-type semiconductor, or the region of detection material is physically adjacent to the n-type semiconductor.

18. The method of manufacturing the device for detecting the item of interest recited in claim 14, wherein the at least one region of semiconductor material is physically located between the substrate and the region of detection material.

19. The method of manufacturing the device for detecting the item of interest recited in claim 14, wherein the detection material comprises a molecularly imprinted polymer.

20. The method of manufacturing the device for detecting the item of interest recited in claim 14, wherein the at least one region of conductive material includes a conductive path that enables at least a portion of an electrical current to bypass the detection material.

21. The method of manufacturing the device for detecting the item of interest recited in claim 14, wherein the conductive material includes at least one conductive material selected from the group consisting of:
   a conductive polymer,
   a carbon ink material, and
   a silver or aluminum ink material.

22. The method of manufacturing the device for detecting the item of interest recited in claim 14, further comprising forming filter above the region of detection material.

\* \* \* \* \*